United States Patent
Iida et al.

(10) Patent No.: US 11,471,387 B2
(45) Date of Patent: Oct. 18, 2022

(54) ORAL CAVITY CARE METHOD AND ORAL CAVITY CARE SYSTEM

(71) Applicant: OPT CREATION INC., Kanagawa (JP)

(72) Inventors: Junichi Iida, Kanagawa (JP); Minoru Koide, Kanagawa (JP)

(73) Assignee: OPT Creation Inc., Kanagawa (JP)

( * ) Notice: Subject to any disclaimer, the term of this patent is extended or adjusted under 35 U.S.C. 154(b) by 0 days.

(21) Appl. No.: 16/956,529

(22) PCT Filed: Dec. 21, 2018

(86) PCT No.: PCT/JP2018/047394
§ 371 (c)(1),
(2) Date: Jun. 19, 2020

(87) PCT Pub. No.: WO2019/124561
PCT Pub. Date: Jun. 27, 2019

(65) Prior Publication Data
US 2021/0137804 A1    May 13, 2021

(30) Foreign Application Priority Data

Dec. 21, 2017 (JP) ................. 2017-245146

(51) Int. Cl.
| A61K 8/22 | (2006.01) |
| A61C 17/02 | (2006.01) |
| A61Q 11/00 | (2006.01) |
| A61C 17/20 | (2006.01) |

(52) U.S. Cl.
CPC ............... *A61K 8/22* (2013.01); *A61C 17/02* (2013.01); *A61C 17/20* (2013.01); *A61Q 11/00* (2013.01); *A61K 2800/74* (2013.01); *A61K 2800/82* (2013.01); *A61K 2800/92* (2013.01)

(58) Field of Classification Search
None
See application file for complete search history.

(56) References Cited

U.S. PATENT DOCUMENTS

| 2009/0047624 A1* | 2/2009 | Tsai | A61C 1/0007 433/119 |
| 2010/0151043 A1* | 6/2010 | Mano | A61P 31/12 424/613 |
| 2012/0092481 A1* | 4/2012 | Dietz | G02B 21/367 348/79 |
| 2016/0045114 A1* | 2/2016 | Dacosta | A61B 5/01 600/476 |
| 2018/0279761 A1* | 10/2018 | Haddad | A46B 5/0095 |

FOREIGN PATENT DOCUMENTS

| JP | 2008168178 A | 7/2008 |
| JP | 201121893 A | 2/2011 |
| JP | 20125658 A | 1/2012 |
| JP | 201255520 A | 3/2012 |
| JP | 201428832 A | 2/2014 |
| WO | 2008072371 A1 | 6/2008 |
| WO | 2016021523 A1 | 2/2016 |

OTHER PUBLICATIONS

Hayakumo et al (Clin Oral Invest, 2013, 17:379-388) (Year: 2013).*
Seki et al (in vivo, 31, 579-583, 2007) (Year: 2007).*
Gupta et al (J Oral Res Rev, 2016, 8:86-91) (Year: 2016).*
Hayakumo et al (Sci Technol Adv Mater, 15, 2014, 1-7) (Year: 2014).*
International Search Report in PCT/JP2018/047394, dated Feb. 19, 2019, 5pp.
Japanese Office Action for Japanese Application No. 2017-245146, dated May 20, 2019, 10pp.

* cited by examiner

*Primary Examiner* — Celeste A Roney (57) ABSTRACT

An oral cavity care method uses a fine ozone bubble liquid, wherein a stock solution of the fine ozone bubble liquid has ozone gas concentration of 100 ppm or more, even if ozone gas concentration of the fine ozone bubble liquid is diluted to 4 ppm or less, the fine ozone bubble liquid has a sterilizing action, the fine ozone bubble liquid has ozone gas concentration of 4 ppm or more after frozen storage for one year or more, and in addition to the sterilizing action, the fine ozone bubble liquid has an odor component decomposition action and an antiviral action.

15 Claims, 4 Drawing Sheets

ORAL CAVITY CARE METHOD AND ORAL CAVITY CARE SYSTEM

RELATED APPLICATIONS

The present application is a National Phase of International Application Number PCT/JP2018/047394, filed Dec. 21, 2018, and claims priority to Japanese Application number 2017-245146, filed Dec. 21, 2017.

TECHNICAL FIELD

The present invention relates to an oral cavity care method and an oral cavity care system, and particularly to an oral cavity care method and an oral cavity care system using a fine ozone bubble liquid.

BACKGROUND ART

Periodontal disease is a general term for diseases that periodontal tissues are infected with periodontal disease bacteria in plaque, and then gingiva swells and bleeds, and teeth fall out. Since periodontal disease bacteria are contained in plaque, it is important to remove plaque, which is a lump of bacteria, in order to prevent periodontal disease. Daily tooth brushing is important to remove plaque, but gargling can also be expected to have the effect of removing plaque. It is also known that gargling with gargle water enhances the effect of removing plaque.

Patent Literature 1 discloses that clinical symptoms of periodontal disease are improved by using a liquid preparation for sterilization or disinfection when gargling, which is containing ozone nanobubble water or oxygen nanobubble water. Further, it is disclosed that the ozone nanobubble water or the oxygen nanobubble water has a sterilizing action or a disinfecting action.

Patent Literature 2 discloses a supply device for supplying dental gargle water comprising an ozone supply means, a dissolved water production apparatus for producing dissolved water in which gas is dissolved, a microbubble generation nozzle for generating microbubbles from the dissolved water supplied from the dissolved water production means, and a container having a supply port for supplying gargle water of microbubbles generated from the microbubble generation nozzle to a cup. Further, it is disclosed that the dental gargle water has an effect of a sterilizing action and an effect of sterilizing bacteria in the oral cavity during treatment of teeth.

In this specification, a bubble having a diameter of 10 μm to tens of μm or less is referred to as a microbubble, a bubble having a diameter of hundreds of nm to 10 μm or less is referred to as a micro-nano bubble, and a bubble having a diameter of hundreds of nm or less is referred to as a nanobubbles.

CITATION LIST

Patent Literature

[Patent Literature 1] Japanese Patent Laid-Open No. 2014-28832
[Patent Literature 2] Japanese Patent Laid-Open No. 2008-168178
[Patent Literature 3] International Patent No. 2016/021523

SUMMARY OF INVENTION

Technical Problem

The liquid preparation for sterilization or disinfection containing ozone nanobubble water or oxygen nanobubble water disclosed in Patent Literature 1 has a sterilizing action or a disinfecting action and improves clinical symptoms of periodontal disease. However, it is difficult to control the nanobubbles due to the difficulty of measurement, and there is no description about preserving methods and concentration controlling methods of the liquid preparation for sterilization or disinfection containing ozone nanobubble water or oxygen nanobubble water. Further, no specific usage of the liquid preparation for sterilization or disinfection containing ozone nanobubble water or oxygen nanobubble water is described other than gargling. In Patent Literature 1, the concentration of molten oxygen in the gas of oxygen nanobubble water is almost the same level as that of normal water.

Further, the device for supplying the dental gargle water disclosed in Patent Literature 2 can sterilize bacteria in the oral cavity during dental treatment by using the gargle water of microbubble as dental gargle water. However, there is no description regarding the concentration of the gargle water of microbubble containing ozone and methods of controlling and storing the gargle water. The usage of the gargle water of microbubble containing ozone is not described other than gargling.

The object of the present invention is to provide an oral cavity care method that enables oral cavity care with a fine ozone bubble liquid, appropriately controls the diameter and concentration of fine bubbles, enables a fine ozone bubble liquid to be stored for a long period of time and has odor component decomposition effect and antiviral effect in addition to the sterilizing effect.

Another object of the present invention is to provide an oral cavity care system that enables oral cavity care with a fine ozone bubble liquid and enables appropriate diagnosis and recording in oral cavity care using an ultrasonic scaler, and to provide a program thereof or a storage medium storing the program.

Solution to Problem

An oral cavity care method using a fine ozone bubble liquid of the first aspect of the present invention is an oral cavity care method using a fine ozone bubble liquid and characterized in that,
wherein a stock solution of the fine ozone bubble liquid has ozone gas concentration of 100 ppm or more,
even if ozone gas concentration of the fine ozone bubble liquid is diluted to 4 ppm or less, the fine ozone bubble liquid has a sterilizing action,
the fine ozone bubble liquid has ozone gas concentration of 4 ppm or more after frozen storage for one year or more, and
in addition to the sterilizing action, the fine ozone bubble liquid has an odor component decomposition action and an antiviral action.

In the present invention (and hereinafter), a liquid generated by using fine ozone bubbles is referred to as a fine ozone bubble liquid.

Further, an oral cavity care method using a fine ozone bubble liquid of the second aspect of the present invention is characterized in that, in the oral cavity care method using the fine ozone bubble liquid of the first aspect, the fine ozone bubble liquid includes at least one type of fine bubbles among micro bubbles, micro nano bubbles and nano bubbles in a production process.

Further, an oral cavity care method using a fine ozone bubble liquid of the third aspect of the present invention is characterized in that, in the oral cavity care method using the fine ozone bubble liquid of the first or second aspect, the fine ozone bubble liquid is produced by containing fine bubbles of ozone gas in water in a production process.

Further, an oral cavity care method using a fine ozone bubble liquid of the fourth aspect of the present invention is characterized in that, in the oral cavity care method using the fine ozone bubble liquid of any one of the first to third aspects, the fine ozone bubble liquid is used as gargle water.

Further, an oral cavity care method using a fine ozone bubble liquid of the fifth aspect of the present invention is characterized in that, in the oral cavity care method using the fine ozone bubble liquid of any one of the first to third aspects, the fine ozone bubble liquid is used for brushing.

Further, an oral cavity care method using a fine ozone bubble liquid of the sixth aspect of the present invention is characterized in that, in the oral cavity care method using the fine ozone bubble liquid of any one of the first to third aspects, the fine ozone bubble liquid is used for treatment with an ultrasonic scaler.

Further, an oral cavity care method using a fine ozone bubble liquid of the seventh aspect of the present invention is characterized in that, in the oral cavity care method using the fine ozone bubble liquid of the sixth aspect, the method comprises the steps of
(1) conducting treatment while supplying the fine ozone bubble liquid,
(2) determining a condition of bacteria in a subgingival margin using a phase contrast microscope, and
(3) recording a diagnosis result in a medical record.

Further, an oral cavity care method using a fine ozone bubble liquid of the eighth aspect of the present invention is characterized in that, in the step (2) in the oral cavity care method using the fine ozone bubble liquid of the seventh aspect, the condition of bacteria is automatically determined and on the basis of the determination, the necessity of additional treatment is determined.

Further, an oral cavity care method using a fine ozone bubble liquid of the ninth aspect of the present invention is characterized in that, in the oral cavity care method using the fine ozone bubble liquid of the seventh or eighth aspect, the medical record in the step (3) is an electronic medical record, and the condition of bacteria determined in the step (2) is automatically recorded in the electronic medical record and taken into account in a next diagnosis.

Further, an oral cavity care method using a fine ozone bubble liquid of the tenth aspect of the present invention is characterized in that, in the oral cavity care method using the fine ozone bubble liquid of any one of the first to ninth aspects, the oral cavity care method is provided for a dental hospital, for treatment of periodontal disease, for preventing periodontal disease or for preventing halitosis.

Further, an oral cavity care method using a fine ozone bubble liquid of the eleventh aspect of the present invention is characterized in that, in the oral cavity care method using the fine ozone bubble liquid of any one of the first to ninth aspects, the oral cavity care method is provided for a nursing care facility, a clinic, or gargling in a facility.

Further, an oral cavity care method using a fine ozone bubble liquid of the twelfth aspect of the present invention is characterized in that, in the oral cavity care method using the fine ozone bubble liquid of any one of the first to ninth aspects, the oral cavity care method is provided for a veterinarian, a pet salon, or a pet for improving halitosis.

Further, an oral cavity care method using a fine ozone bubble liquid of the thirteenth aspect of the present invention is characterized in that, in the oral cavity care method using the fine ozone bubble liquid of any one of the first to ninth aspects, the oral cavity care method is provided for beauty, health, sports, preventing health deterioration, or health promotion.

Further, an oral cavity care method using a fine ozone bubble liquid of the fourteenth aspect of the present invention is characterized in that, in the oral cavity care method using the fine ozone bubble liquid of any one of the first to ninth aspects, the oral cavity care method is provided for preventing periodontal disease in house, for gargling in house, or for household use.

Further, an oral cavity care system using a fine ozone bubble liquid of the fifteenth aspect of the present invention is an oral cavity care system using a fine ozone bubble liquid, characterized in that the system comprises:
(1) a means for determining a condition of bacteria in a subgingival margin using a phase contrast microscope after treatment while supplying the fine ozone bubble liquid.
(2) a means for recording a diagnosis result in an electronic medical record,
(3) a means for displaying information of the electronic medical record.

Further, an oral cavity care system using a fine ozone bubble liquid of the sixteenth aspect of the present invention is characterized in that, in the means (1) in an oral cavity care system using the fine ozone bubble liquid of the fifteenth aspect of the present invention, the condition of bacteria is automatically determined and on the basis of the determination, the necessity of additional treatment is determined and displayed on the means for displaying information Further, an oral cavity care system using a fine ozone bubble liquid of the seventeenth aspect of the present invention is characterized in that, in the oral cavity care system using the fine ozone bubble liquid of the fifteenth or sixteenth aspect of the present invention, the condition of bacteria determined in the means (1) is automatically recorded in the electronic medical record and taken into account in a next diagnosis.

Further, an oral cavity care system using a fine ozone bubble liquid of the eighteenth aspect of the present invention is characterized in that, in the oral cavity care system using the fine ozone bubble liquid of any one of the fifteenth to seventeenth aspects of the present invention, the information displayed in (3) is supplied to a means for removing tartar or plaque with an ultrasonic scaler while supplying the fine ozone bubble liquid to the tip of the ultrasonic scaler.

Further, an oral cavity care system using a fine ozone bubble liquid of the nineteenth aspect of the present invention is characterized in that, in the oral cavity care system using the fine ozone bubble liquid of any one of the fifteenth to eighteenth aspects of the present invention, a stock solution of the fine ozone bubble liquid has ozone gas concentration of 100 ppm or more,
even if ozone gas concentration of the fine ozone bubble liquid is diluted to 4 ppm or less, the fine ozone bubble liquid has a sterilizing action,
the fine ozone bubble liquid has ozone gas concentration of 4 ppm or more after frozen storage for one year or more, and in addition to the sterilizing action, the fine ozone bubble liquid has an odor component decomposition action and an antiviral action.

Further, an oral cavity care system using a fine ozone bubble liquid of the twentieth aspect of the present invention is characterized in that, in the oral cavity care system using the fine ozone bubble liquid of any one of the fifteenth to nineteenth aspects of the present invention, the fine ozone bubble liquid includes at least one type of fine bubbles among micro bubbles, micro nano bubbles and nano bubbles in a production process.

Further, an oral cavity care system using a fine ozone bubble liquid of the twenty-first aspect of the present invention is characterized in that, in the oral cavity care system using the fine ozone bubble liquid of any one of the fifteenth to twentieth aspects of the present invention, the fine ozone bubble liquid is produced by containing fine bubbles of ozone gas in water in a production process.

Further, an oral cavity care system using a fine ozone bubble liquid of the twenty-second aspect of the present invention is characterized in that, in the oral cavity care system using the fine ozone bubble liquid of any one of the fifteenth to twenty-first aspects of the present invention, the oral cavity care system is provided for a dental hospital, for treatment of periodontal disease, for preventing periodontal disease or for preventing halitosis.

Further, an oral cavity care system using a fine ozone bubble liquid of the twenty-third aspect of the present invention is characterized in that, in the oral cavity care system using the fine ozone bubble liquid of any one of the fifteenth to twenty-first aspects of the present invention, the oral cavity care system is provided for a nursing care facility, a clinic, or gargling in a facility.

Further, an oral cavity care system using a fine ozone bubble liquid of the twenty-fourth aspect of the present invention is characterized in that, in the oral cavity care system using the fine ozone bubble liquid of any one of the fifteenth to twenty-first aspects of the present invention, the oral cavity care system is provided for a veterinarian, a pet salon, or a pet for improving halitosis.

Further, an oral cavity care system using a fine ozone bubble liquid of the twenty-fifth aspect of the present invention is characterized in that, in the oral cavity care system using the fine ozone bubble liquid of any one of the fifteenth to twenty-first aspects of the present invention, the oral cavity care system is provided for beauty, health, sports, preventing health deterioration, or health promotion.

Further, a program of the twenty-sixth aspect of the present invention is characterized in that the program operates a computer as each of the means in the oral cavity care system using the fine ozone bubble liquid of any one of fifteenth to twenty-fifth aspect of the present invention.

Further, a storage medium of the twenty-seventh aspect of the present invention is characterized in that the storage medium stores the program of the twenty-sixth aspect of the present invention.

Advantageous Effects of Invention

According to the oral cavity care method using the fine ozone bubble liquid of the first aspect of the present invention, an oral cavity care can be performed with a fine ozone bubble liquid. A stock solution of the fine ozone bubble liquid has ozone gas concentration of 100 ppm or more and even if ozone gas concentration of the fine ozone bubble liquid is diluted to 4 ppm or less, the fine ozone bubble liquid has a sterilizing action. Therefore, the concentration of fine bubbles can be appropriately controlled. Further, the fine ozone bubble liquid has ozone gas concentration of 4 ppm or more after frozen storage for one year or more. Therefore, the fine ozone bubble liquid can be stored for a long period of time. Furthermore, an oral cavity care method with an odor component decomposition action and an antiviral action in addition to the sterilizing action can be provided.

According to the oral cavity care method using the fine ozone bubble liquid of the second aspect of the present invention, at least one type of fine bubbles among micro bubbles, micro nano bubbles and nano bubbles can be used as fine bubbles. Therefore, various sizes of fine bubbles can be used.

According to the oral cavity care method using the fine ozone bubble liquid of the third aspect of the present invention, the fine ozone bubble liquid is produced by containing fine bubbles of ozone gas in water in a production process. Therefore, it is safe for the human body and does not have a harmful effect on the environment. Additionally, since water is used and other chemicals are not used, the fine ozone bubble liquid can be produced at low cost.

According to the oral cavity care method using the fine ozone bubble liquid of the fourth aspect of the present invention, by using the fine ozone bubble liquid as gargle water, the oral cavity care having a high sterilizing effect can be easily performed.

According to the oral cavity care method using the fine ozone bubble liquid of the fifth aspect of the present invention, the fine ozone bubble liquid can be used for brushing. Therefore, the oral cavity care having a high sterilizing effect can be easily performed in house. As a result, a prevention effect for periodontal disease and halitosis can be obtained.

According to the oral cavity care method using the fine ozone bubble liquid of the sixth aspect of the present invention, by using the fine ozone bubble liquid for treatment with an ultrasonic scaler, removing tartar or plaque with the ultrasonic scaler and sterilizing periodontal bacteria can be performed at the same time. Therefore, effective treatment can be performed without adding a treatment procedure. In particular, it is effective for treating or preventing periodontal disease.

According to the oral cavity care method using the fine ozone bubble liquid of the seventh aspect of the present invention, in the step of conducting treatment while supplying the fine ozone bubble liquid, the fine ozone bubble liquid can be supplied appropriately. Further, in this step, for example, if an ultrasonic scaler is used, it is also possible to remove tartar or plaque with the ultrasonic scaler while supplying the fine ozone bubble liquid to the tip of the ultrasonic scaler. Furthermore, by using a phase contrast microscope, the condition such as the number and movement of bacteria can be clearly confirmed. Therefore, the condition of bacteria can be reliably determined. Furthermore, a diagnosis result including the condition of bacteria can be recorded in a medical record. Therefore, appropriate treatment can be performed by taking into account the description content of the medical record in a next diagnosis.

According to the oral cavity care method using the fine ozone bubble liquid of the eighth aspect of the present invention, in the step (2), the condition of bacteria can be automatically determined. Therefore, the determination can be appropriately performed on the basis of stable determination criteria. As a result, the necessity of additional treatment can be reliably determined.

According to the oral cavity care method using the fine ozone bubble liquid of the ninth aspect of the present invention, the medical record in the step (3) is an electronic medical record. Therefore, the management of the medical record can be appropriately performed without trouble. Furthermore, the condition of bacteria determined in the step (2) is automatically recorded in the electronic medical record. Therefore, the diagnosis result including the condition of bacteria can be recorded in the electronic medical record reliably and without trouble.

According to the oral cavity care method using the fine ozone bubble liquid of the tenth aspect of the present invention, the oral cavity care method can be provided for a dental hospital, for treatment of periodontal disease, for preventing periodontal disease or for preventing halitosis. Therefore, in particular, an oral cavity care method suitable for a dental hospital can be provided.

According to the oral cavity care method using the fine ozone bubble liquid of the eleventh aspect of the present invention, the oral cavity care method can be provided for a nursing care facility, a clinic, or gargling in a facility. Therefore, in particular, an oral cavity care method suitable for a nursing care facility and a clinic can be provided.

According to the oral cavity care method using the fine ozone bubble liquid of the twelfth aspect of the present invention, the oral cavity care method can be provided for a veterinarian, a pet salon, or a pet for improving halitosis. Therefore, in particular, an oral cavity care method suitable for a veterinarian or a pet salon can be provided.

According to the oral cavity care method using the fine ozone bubble liquid of the thirteenth aspect of the present invention, the oral cavity care method can be provided for beauty, health, sports, preventing health deterioration, or health promotion. Therefore, in particular, an oral cavity care method suitable for beauty, health or sports can be provided.

According to the oral cavity care method using the fine ozone bubble liquid of the fourteenth aspect of the present invention, the oral cavity care method can be provided for preventing periodontal disease in house, for gargling in house, or for household use. Therefore, in particular, an oral cavity care method suitable for household use can be provided.

According to the oral cavity care system using the fine ozone bubble liquid of the fifteenth aspect of the present invention, an oral cavity care can be performed with a fine ozone bubble liquid. By a means for determining a condition of bacteria in a subgingival margin using a phase contrast microscope after treatment while supplying the fine ozone bubble liquid, the fine ozone bubble liquid can be appropriately supplied. Additionally, by using a phase contrast microscope, the condition such as the number and movement of bacteria can be clearly confirmed. Therefore, the condition of bacteria can be reliably determined. When performing treatment while supplying the fine ozone bubble liquid, for example, if an ultrasonic scaler is used, tartar or plaque can be removed with the ultrasonic scaler while supplying the fine ozone bubble liquid to the tip of the ultrasonic scaler. Further, a diagnosis result including the condition of bacteria can be recorded in an electronic medical record. Therefore, treatment can be appropriately performed by taking into account the description content of the electronic medical record in a next diagnosis. Further, by providing a means for displaying information of the electronic medical record, a doctor, a dental hygienist or the like (hereinafter, referred to as "doctors or the like") can easily see the information of the electronic medical record.

According to the oral cavity care system using the fine ozone bubble liquid of the sixteenth aspect of the present invention, in the means of (1), the condition of bacteria is automatically determined, and on the basis of the determination, the necessity of additional treatment is determined and displayed on the means for displaying information. Therefore, the determination can be appropriately performed on the basis of stable determination criteria. As a result, the necessity of additional treatment can be reliably determined. Further, by displaying the information on the means for displaying information, doctors or the like can easily see the information regarding the necessity of the additional treatment.

According to the oral cavity care system using the fine ozone bubble liquid of the seventeenth aspect of the present invention, the condition of bacteria determined in the means (1) is automatically recorded in the electronic medical record. Therefore, the management of the electronic medical record can be appropriately performed without trouble. Additionally, the diagnosis result including the condition of bacteria can be recorded in the electronic medical record reliably and without trouble and can be taken into account in a next diagnosis. As a result, doctors or the like can appropriately grasp the state of past treatment.

According to the oral cavity care system using the fine ozone bubble liquid of the eighteenth aspect of the present invention, the information displayed in (3) is supplied to a means for removing tartar or plaque with an ultrasonic scaler while supplying the fine ozone bubble liquid to the tip of the ultrasonic scaler. Therefore, on the basis of the information in the electronic medical record or the information regarding the necessity of the additional treatment, the means for removing tartar or plaque with an ultrasonic scaler can be appropriately controlled. For example, the output of the ultrasonic scaler and the amount of the fine ozone bubble liquid supplied to the ultrasonic scaler can be appropriately controlled.

According to the oral cavity care system using the fine ozone bubble liquid of the nineteenth aspect of the present invention, an oral cavity care can be performed with a fine ozone bubble liquid. A stock solution of the fine ozone bubble liquid has ozone gas concentration of 100 ppm or more and even if ozone gas concentration of the fine ozone bubble liquid is diluted to 4 ppm or less, the fine ozone bubble liquid has a sterilizing action. Therefore, the concentration of fine bubbles can be appropriately controlled. Further, the fine ozone bubble liquid has ozone gas concentration of 4 ppm or more after frozen storage for one year or more. Therefore, the fine ozone bubble liquid can be stored for a long period of time. Furthermore, an oral cavity care system with an odor component decomposition action and an antiviral action in addition to the sterilizing action can be provided.

According to the oral cavity care system using the fine ozone bubble liquid of the twentieth aspect of the present invention, at least one type of fine bubbles among micro bubbles, micro nano bubbles and nano bubbles can be used as the fine ozone bubble liquid. Therefore, various sizes of fine bubbles can be used.

According to the oral cavity care system using the fine ozone bubble liquid of the twenty-first aspect of the present invention, the fine ozone bubble liquid is produced by containing fine bubbles of ozone gas in water in a production process. Therefore, it is safe for the human body and does not have a harmful effect on the environment. Additionally, since water is used and other chemicals are not used, the fine ozone bubble liquid can be produced at low cost.

According to the oral cavity care system using the fine ozone bubble liquid of the twenty-second aspect of the present invention, the oral cavity care system can be provided for a dental hospital, for treatment of periodontal disease, for preventing periodontal disease or for preventing halitosis. Therefore, in particular, an oral cavity care method suitable for a dental hospital can be provided.

According to the oral cavity care system using the fine ozone bubble liquid of the twenty-third aspect of the present invention, the oral cavity care system can be provided for a nursing care facility, a clinic, or gargling in a facility. Therefore, in particular, an oral cavity care method suitable for a nursing care facility and a clinic can be provided.

According to the oral cavity care system using the fine ozone bubble liquid of the twenty-fourth aspect of the present invention, the oral cavity care system can be provided for a veterinarian, a pet salon, or a pet for improving halitosis. Therefore, in particular, an oral cavity care method suitable for a veterinarian or a pet salon can be provided.

According to the oral cavity care system using the fine ozone bubble liquid of the twenty-fifth aspect of the present invention, the oral cavity care system can be provided for beauty, health, sports, preventing health deterioration, or health promotion. Therefore, in particular, an oral cavity care method suitable for beauty, health or sports can be provided.

According to the program of the twenty-sixth aspect of the present invention, a program having the same effects as the effect of any one of the fifteenth to twenty-fifth aspects can be provided.

According to the storage medium of the twenty-seventh aspect of the present invention, a storage medium storing a program of the twenty-sixth aspect can be provided.

DESCRIPTION OF EMBODIMENTS

Hereinafter, an oral cavity care method using a fine ozone bubble liquid, an oral cavity care system using a fine ozone bubble liquid, a program thereof, and a storage medium storing the program according to embodiments of the present invention will be described in detail with reference to drawings. However, embodiments described below exemplify an oral cavity care method using a fine ozone bubble liquid, an oral cavity care system using a fine ozone bubble liquid, a program thereof, and a storage medium storing the program in order to embody the technical concept of the present invention. Thus, it is to be understood that the invention is not limited to these embodiments, and is equally applicable to other embodiments within the scope of the claims.

Embodiment 1

An oral cavity care method using a fine ozone bubble liquid and an oral cavity care system using a fine ozone bubble liquid according to embodiment 1 will be described with reference to FIGS. 1 to 6D.

Figure 1:
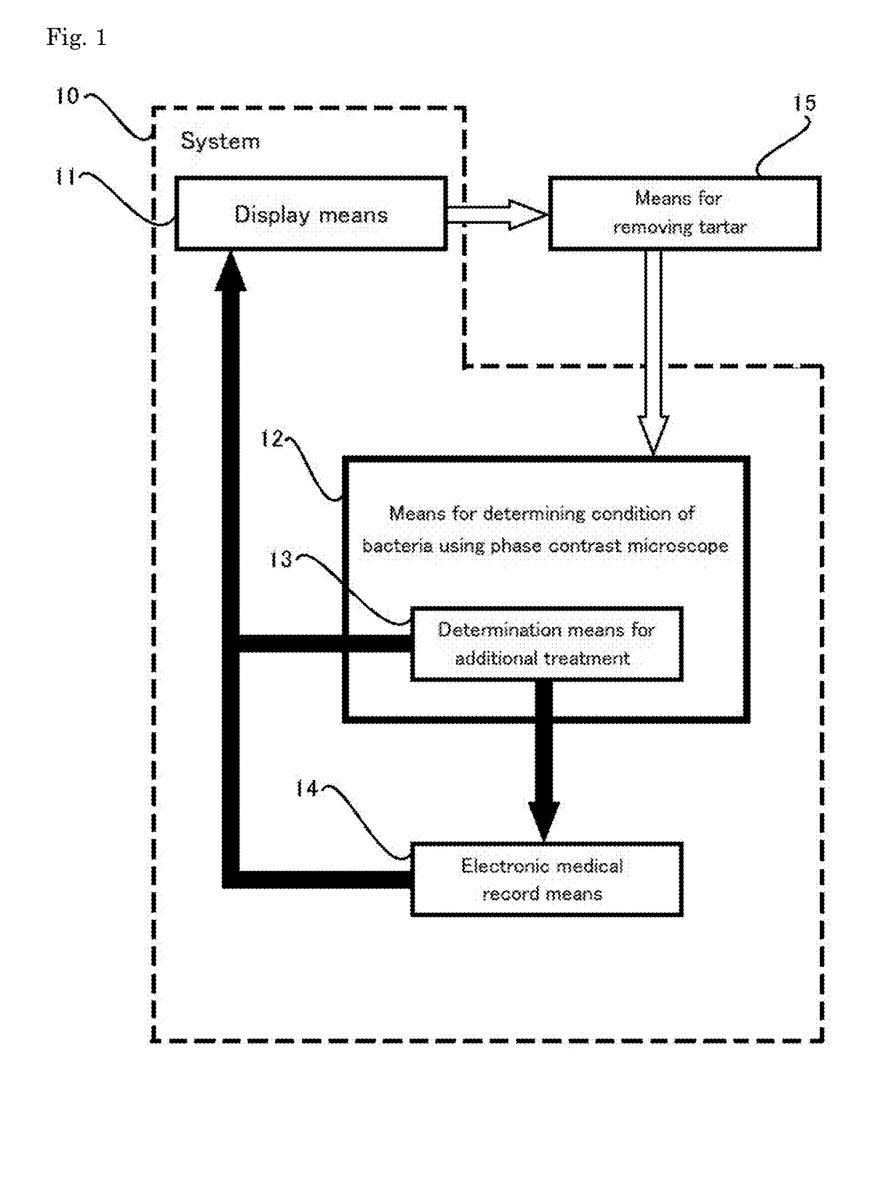
FIG. 1 is a block diagram of a dental treatment system.

FIG. 1 is a block diagram of an oral cavity care system using a fine ozone bubble liquid according to embodiment 1. A system 10 includes a display means 11, a means 12 for determining a condition of bacteria using a phase contrast microscope, and an electronic medical record means 14. Electronic medical record data of medical examination is stored every time in the electronic medical record means 14, and the information of the electronic medical record stored in the electronic medical record means 14 can be displayed by the display means 11 at the time of a diagnosis.

Taking the information of the electronic medical record into account, doctors or the like remove the tartar or plaque of the patient by a means for removing tartar or plaque with an ultrasonic scaler using the fine ozone bubble liquid. The tip of the ultrasonic scaler is equipped with a chip for contacting the tooth to remove tartar or plaque. This chip vibrates about 30,000 times per second, for example, with a piezoelectric element to remove tartar or plaque. The ultrasonic scaler is provided with a tank for storing the fine ozone bubble liquid, and the fine ozone bubble liquid is supplied from the tank to the end of the chip of the ultrasonic scaler.

The ultrasonic scaler is configured so that the suppling amount of the fine ozone bubble liquid can be adjusted. Further, the ultrasonic scaler is configured so that its output can be adjusted. Therefore, doctors or the like can adjust the supplying amount of the fine ozone bubble liquid and the output of the ultrasonic scaler according to the state of the treatment for removing plaque while taking into account the information of the electronic medical record displayed on the display means. For example, by reducing the output of the ultrasonic scaler, it is possible to reduce the pain during the treatment for removing tartar or plaque, and to reduce the damage on the tooth surface.

In addition to the sterilizing effect, the fine ozone bubble liquid has an odor component decomposition effect and an antiviral effect. Therefore, by performing the usual treatment for removing tartar or plaque with the ultrasonic scaler, at the same time, sterilization in a subgingival margin can be performed, and moreover, an odor component decomposition effect and an antiviral effect can be obtained.

After the removal of tartar or plaque by a means 15 for removing tartar or plaque with the ultrasonic scaler using the fine ozone bubble liquid is completed, by the means 12 for determining the condition of bacteria using the phase contrast microscope, in a sample (plaque) collected from the subgingival margin, the condition such as the number and movement of bacteria is confirmed and the condition of bacteria is determined. The phase contrast microscope applies the principle of diffraction gratings to detect a phase shift as a contrast in an image. The phase contrast microscope has a structure in which a dedicated phase difference capacitor and phase difference objective lens are added to the optical microscope. Since the specimen can be observed without being dyed, the phase contrast microscope is often used for observing biological cells and for clinical examination.

The specimen is observed with the phase contrast microscope and as the number of actively moving bacteria is smaller or the bacteria are less moving, the higher sterilizing effect is recognized. In a determination means 13 for automatically determining the necessity of additional treatment, the movement of bacteria observed by the phase contrast microscope is photographed with a camera as a moving image and recognized to automatically observe the movement of bacteria. Then, it is determined whether the sterilizing effect is recognized or not. Alternatively, the degree of the sterilizing effect is further determined. In this case, the degree of the sterilizing effect may be expressed in a plurality of stages or as a numerical value. Further, it is possible to automatically analyze the sterilizing effect and present the necessity for additional treatment and the contents of the treatment.

In addition, when automatically analyzing the sterilizing effect, an appropriate arithmetic device such as a personal computer or a tablet terminal can be used. Further, AI can be used when image recognition is performed from an image captured as a moving image, the sterilizing effect is analyzed, and the necessity of additional treatment and the content of the treatment are presented. For example, it is possible to construct a neural network using a data set regarding an image, a sterilizing effect and a treatment content to output an evaluation of the sterilizing effect and an appropriate treatment content from the input image.

The determination result made by the determination means 13 for automatically determining the necessity of additional treatment is sent to the electronic medical record means 14 and recorded in the electronic medical record. As information stored in the electronic medical record, only the final determination result by the determination means 13 may be stored, and in addition to this, for example, data in analyzing the movement of bacteria and a moving image capturing the movement of bacteria may be included.

The determination result of the determination means 13 is also sent to the display means 11, and the determination result is displayed on the display means 11. At this time, as information to be displayed, only the final determination result by the determination means 13 may be included, and in addition to this, for example, data in analyzing the movement of bacteria and a moving image capturing the movement of bacteria may be included. Doctors or the like determine the treatment policy by taking the information displayed on the display means 11 into account, that is, whether or not the sterilizing effect is recognized, the degree of the sterilizing effect, the necessity of additional treatment, and the content of the treatment.

According to the system 10 of FIG. 1, by using the fine ozone bubble liquid for treatment with an ultrasonic scaler, removing tartar or plaque with the ultrasonic scaler and sterilizing periodontal bacteria can be performed at the same time. Therefore, effective treatment can be performed without adding a treatment procedure. In particular, it is effective for treating or preventing periodontal disease.

Further, the fine ozone bubble liquid can be appropriately supplied in a process of removing tartar or plaque with an ultrasonic scaler while supplying the fine ozone bubble liquid to the tip of the ultrasonic scaler. Furthermore, by using a phase contrast microscope, the condition such as the number and movement of bacteria can be clearly confirmed. Therefore, the condition of bacteria can be reliably determined. Furthermore, a diagnosis result including the condition of bacteria can be recorded in a medical record. Therefore, appropriate treatment can be performed by taking into account the description content of the medical record in a next diagnosis.

Further, the condition of bacteria can be automatically determined. Therefore, the determination can be appropriately performed on the basis of stable determination criteria. As a result, the necessity of additional treatment can be reliably determined.

Furthermore, by using an electronic medical record, the management of the medical record can be appropriately performed without trouble. In addition, the condition of bacteria determined by using a phase contrast microscope is automatically recorded in the electronic medical record. Therefore, the diagnosis result including the condition of bacteria can be recorded in the electronic medical record reliably and without trouble. And the result can be referred to in a next diagnosis.

In FIG. 1, the means 15 for removing tartar or plaque with an ultrasonic scaler using the fine ozone bubble liquid is described as a means outside the system 10, but the present invention is not limited to this configuration. For example, it is possible to incorporate the means 15 for removing tartar or plaque with the ultrasonic scaler using the fine ozone bubble liquid into the system 10. In this case, the means 15 for removing tartar or plaque with the ultrasonic scaler using the fine ozone bubble liquid can automatically adjusts, for example, the output of the ultrasonic scaler or the amount of the fine ozone bubble liquid on the basis of the information from the display means 11.

Since the display means includes information from the electronic medical record means 14 and information from the determination means 13 for automatically determining the necessity of additional treatment, the output of the ultrasonic scaler and the amount of fine ozone bubble liquid required for the treatment can be set appropriately. For example, when the determination means 13 sends a determination result indicating that sterilization is insufficient, the output of the ultrasonic scaler can be increased or the amount of the fine ozone bubble liquid can be increased. Also, for example, if it is known from the information in the electronic medical record that the sterilizing effect can be easily obtained, the output of the ultrasonic scaler can be set to be small, or the amount of the fine ozone bubble liquid can be adjusted to be small. The output of the ultrasonic scaler and the amount of the fine ozone bubble liquid may be determined by doctors or the like before being automatically changed.

Next, a method for producing the fine ozone bubble liquid will be described. As a method for producing a fine bubble liquid, for example, ejector method, cavitation method, swirl-type liquid flow method, high pressure dissolution method and the like are known, but in the present invention, known technique, which is described in the above-mentioned Patent Literature 3 (WO2016/021523), is applied to produce the fine ozone bubble liquid.

Hereinafter, a method for producing the fine ozone bubble liquid will be described. An inorganic aqueous solution stored in a storage tank is sucked with ozone by a pump. Then, the inorganic aqueous solution and ozone are mixed and flown into a closed container. The inorganic aqueous solution mixed with ozone is agitated in the closed container and passes through a bubble generation nozzle to generate bubbles.

The bubble generating nozzle has a nozzle body having a communication hole and a large-diameter stirring chamber continuous with the communication hole, and a cartridge body having a bottom and a cylindrical shape. The open side of the cartridge body is fitted to the communication hole of the nozzle body. A fine mesh member and an orifice having a plurality of small holes are sequentially provided on the open side of the cartridge body, and a pressure release chamber is provided between the bottom surface of the cartridge body and the mesh member. On the other hand, a plurality of through holes having a diameter smaller than the small holes of the orifices, which communicate between the pressure release chamber and the stirring chamber, are provided on the side wall on the bottom surface side of the cartridge body.

When the inorganic aqueous solution mixed with ozone passes through the orifice, the pressure is released, thereby fine bubbles of ozone are generated, and the fine bubbles are further miniaturized by the mesh member. The pressure of the inorganic aqueous solution containing ozone injected into the pressure release chamber is released in the pressure release chamber. Thus, the fine bubbles are further generated and collide with the bottom surface of the pressure release chamber, thereby the bubbles are further miniaturized. Then, when the inorganic aqueous solution containing ozone is jetted into the stirring chamber through the through holes, finer bubbles are generated due to the release of pressure, and the bubbles are further miniaturized by the stirring action in the stirring chamber and jetted from the tip of the nozzle into the reservoir. In this way, the inorganic aqueous solution containing ozone is continuously sucked by the pump and fine bubbles are generated in the nozzle, thereby the fine ozone bubble liquid is generated in the storage tank.

By adjusting time for which the inorganic aqueous solution containing ozone is circulated through the nozzle with the pump, the concentration of the fine ozone bubble liquid can be appropriately adjusted. In the present invention, the concentration of ozone gas in the fine ozone bubble liquid is adjusted to 100 ppm or more.

The size of the fine bubbles can be adjusted by adjusting the specifications such as the dimensions of each part of the orifice, the mesh member, the through holes, the pressure release chamber and the stirring chamber, or by adjusting the temperature by providing a heat exchanger. In the present invention, at least one type of fine bubbles among micro bubbles having a diameter of 10 μm to tens of μm or less, micro nano bubbles having a diameter of hundreds of nm to 10 μm or less, and nano bubbles having a diameter of hundreds of nm or less can be generated.

As an inorganic aqueous solution, those containing at least one kind of ion selected from sodium ion, magnesium ion, potassium ion and calcium ion, and those containing an inorganic component such as bittern are exemplified. However, the inorganic aqueous solution is not limited thereto and may be pure water, purified water or normal water.

Figure 2:
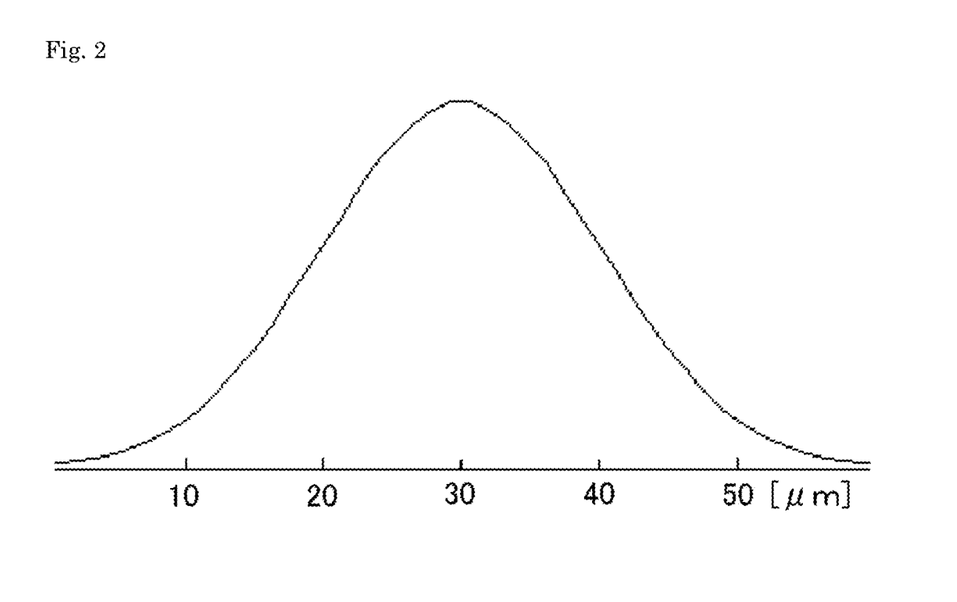
FIG. 2 is a conceptual diagram showing the distribution of diameters of fine bubbles in a fine ozone bubble liquid.

FIG. 2 is a conceptual diagram showing the distribution of diameters of fine bubbles of the fine ozone bubble liquid. The distribution of diameters of the fine bubble particles of the fine ozone bubble liquid is a normal distribution, preferably the fine bubbles include the bubbles having a diameter of 50 μm or less at least 50% of all the bubbles. More preferably, the fine bubbles includes bubbles having a diameter of 50 μm or less at least 90%. Further, the fine bubbles also include bubbles having a diameter of 10 μm or less. Furthermore, it is also possible to use bubbles having a diameter of several hundreds nm or less. Most periodontal disease bacteria are 1 μm or less, but since fine bubbles are sufficiently small with respect to the size of periodontal disease bacteria, it is possible to spread fine bubble particles to the site where periodontal disease bacteria are present.

Although a known measuring device for measuring the distribution of the particle size is used for measuring the particle size of the bubbles, it is currently difficult to accurately grasp the distribution of nanobubbles of 100 nm or less. If nanobubble measurement technology advances in the future, finer nanobubbles can be accurately measured, and therefore it can be expected that the particle size distribution of nanobubbles of 100 nm or less, particularly 50 nm or less can be accurately grasped. In this case, it is expected that the proportion of bubbles having a diameter of 50 μm or less and/or bubbles having a diameter of 10 μm or less in all the bubbles is further increased.

The fine bubbles of the fine ozone bubble liquid may include micro bubbles, micro nano bubbles, or nano bubbles as described above. Further, FIG. 2 shows an example of the diameter distribution of the fine bubble particles of the fine ozone bubble liquid, and the diameter distribution of the fine bubble particles of the fine ozone bubble liquid of the present invention is not limited to this example. For example, it is possible to change the center value of the normal distribution by adjusting the bubbles to be generated, by adjusting the specifications such as the dimensions of each part of the nozzle or by adjusting the temperature by providing a heat exchanger. Further, for example, the distribution may be other than the normal distribution.

Figure 3:
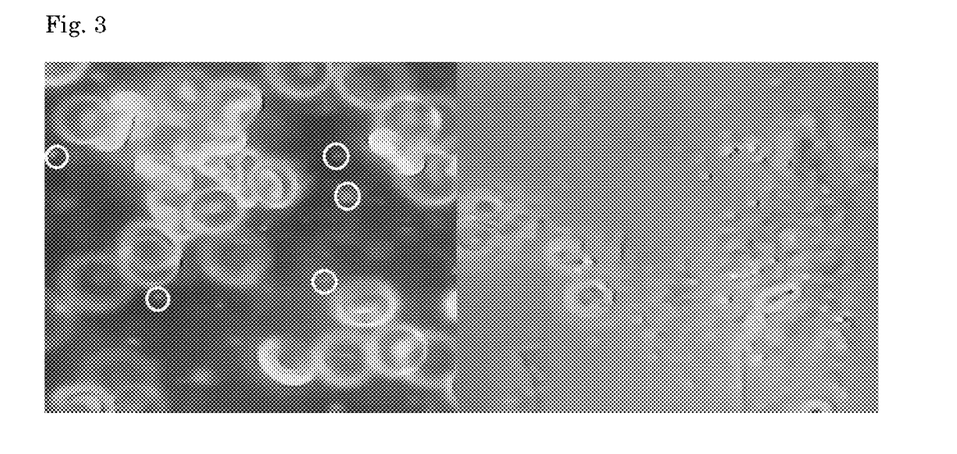
FIG. 3 is a picture of a phase contrast microscope.

FIG. 3 shows two pictures of phase contrast micrographs for confirming the sterilizing effect of the fine ozone bubble liquid of embodiment 1. The left side is a photograph in which purified water is used together with an ultrasonic scaler, and the right side is a photograph in which the fine ozone bubble liquid is used together with an ultrasonic scaler. In a case of the photograph on the right side, a liquid, which is produced by mixing a 10 times diluted liquid of a stock solution of the fine ozone bubble liquid with purified water in a production process, is used. In both cases, a sample was taken from a subgingival margin, transferred to a preparation and set on a phase contrast microscope to observe the cell condition.

In the photograph on the left side of FIG. 3, cells that move around actively are marked with white circles. The disk-shaped substances shown in the photograph are red blood cells. In the photograph on the left, it can be seen that many cells are actively moving around. On the other hand, in the photograph on the right side of FIG. 2, white circles are not added because there are no cells that move around actively. In the photograph on the right side of FIG. 2, only slightly moving cells were observed partially, but bacteria did not move on the whole, and the sterilizing effect was observed.

Hereinafter, the characteristics of the fine ozone bubble liquid of Embodiment 1 will be described. The fine bubbles of the fine ozone bubble liquid are charged and repel each other. Thus, the fine bubbles are not combined with each other, and highly dense fine bubbles can be generated. In addition, the rising speed of the fine bubbles of the fine ozone bubble liquid is very low and the fine bubbles can stay in water for a long time. Therefore, the fine ozone bubble liquid can be stored for a long period of time. For example, the ozone concentration of the fine ozone bubble liquid is maintained at 100 ppm or more as measured by the KI method even after 6 months or more have passed since the production at normal temperature. The fine ozone bubble liquid can also be frozen and stored. When the stock solution of the fine ozone bubble liquid (100 ppm or more) was stored at −20° C. for 1 year, the ozone concentration was maintained at about 4 ppm. As will be described later, from the viewpoint of sterilizing effect, in both cases of normal temperature storage and frozen storage, only 0.1 ppm or more is needed for the ozone concentration of the fine ozone bubble liquid, and preferably, the ozone concentration may be 1 ppm or more, and more preferably, the concentration may be 4 ppm or more. The ozone concentration after storage for 6 months at normal temperature does not necessarily have to be maintained at 100 ppm or more, and is preferably 4 ppm or more, more preferably 10 ppm or more, more preferably 50 ppm or more, and further preferably 80 ppm or more.

The fine ozone bubble liquid can inactivate bacteria and viruses and also decompose harmful chemical substances.

Furthermore, due to the synergistic effect with the effect of sterilization and deodorization by ozone contained in the fine ozone bubble liquid, effects such as sterilization and deodorization are more obtained. As a result, if the fine ozone bubble liquid is used, bacteria and viruses are inactivated, and sterilization and deodorizing effects are obtained.

Further, when cavitation occurs due to the ultrasonic vibration of the ultrasonic scaler, the sterilizing effect of the fine ozone bubble liquid can be further enhanced. Therefore, by supplying the fine ozone bubble liquid and using the ultrasonic scaler, a high sterilizing effect, which is effective against viruses, is exhibited, and a deodorizing effect is also exhibited.

Further, the fine ozone bubble liquid of Embodiment 1 also has a sterilizing effect for
(1) multi-drug resistant *Staphylococcus aureus* (*Staphylococcus aureus*), vancomycin-resistant enterococci (*Enterococcus faecalis, E. faecium*), multi-drug resistant *Pseudomonas aeruginosa* (*Pseudonomas aeruginosa*) as resistant bacteria,
(2) Pg (*Porphyromonas gingivalis*), Pi (*Prevotella intermedia*), Aa (*Aggregatibacter actinomycetemcomitans*), Fn (*Fusobacterium nucleatum*) as pathogenic bacteria of periodontal disease, and
(3) *Streptococcus mutans* as cariogenic bacteria.

Even if ozone gas concentration of the fine ozone bubble liquid of embodiment 1 is diluted to 4 ppm, the fine ozone bubble liquid has a sterilizing action. Further, the sterilizing effect was also obtained when diluted to 0.1 ppm. Table 1 shows the effect by the fine ozone bubble liquid in a sterilization test. EC represents *Escherichia coli* (Gram-negative bacterium), SA represents *Staphylococcus aureus* (Gram-positive bacterium), BS represents *Bacillus subtilis* (spore), CA represents candidiasis (yeast-like fungi), and AF represents aflatoxin (fungi). EC, SA, BS and CA were highly sensitive and exhibited a sterilizing effect at a concentration of 0.1%. AF has high resistance, but exhibited a sterilizing effect at a concentration of 1%. Since the ozone gas concentration of the stock solution of the fine ozone bubble liquid is 100 ppm or more, only 0.1 ppm or more is needed for the ozone gas concentration of the fine ozone bubble liquid. The ozone gas concentration is preferably 1 ppm or more, and more preferably 4 ppm or more.

TABLE 1

| | Concentration of solution (%) | | | | |
|---|---|---|---|---|---|
| | 100 | 10 | 1 | 0.1 | 0 |
| EC | 0 | 0 | 0 | 0 | $10^7$ |
| SA | 0 | 0 | 0 | 0 | $10^6$ |
| BS | 0 | 0 | 0 | 0 | $10^5$ |
| CA | 0 | 0 | 0 | 0 | $10^5$ |
| AF | 0 | 0 | 0 | $10^4$ | $10^4$ |

Table 2 shows the effect of the fine ozone bubble liquid in an antivirus test. In Table 2, the effect on avian influenza virus H5N3 was tested. As materials, avian influenza virus H5N3 and 10-day-old embryonated chicken eggs were used. First, 0.1 mL of the virus, which is diluted to 10 times with sterilized phosphate buffered saline (PBS), is added to 0.9 mL of the fine ozone bubble liquid of Embodiment 1, which is diluted to 100 times with sterilized PBS, to react for 10 minutes. Next, this mixed solution was diluted stepwise by 10 times, and 0.1 mL of each diluted step of the solution was inoculated into the chorioallantoic cavities of three embryonated chicken eggs. Next, after cultivating the embryonated chicken eggs at 37° C. for 48 hours, the presence or absence of virus growth was confirmed by a hemagglutination test, and the virus infectivity titer was calculated by the method of Reed and Muench. In Table 2, the cumulative positive was 0 in all cases, and the cumulative positive rate was 0 in all cases, and the virus infectivity titer of the fine ozone bubble liquid was $10^{-0.5}$ $EID_{50}/0.1$ mL>.

TABLE 2

| Dilution | a | b | c | Cumulative negative | Cumulative positive | Cumulative positive rate |
|---|---|---|---|---|---|---|
| 0 | — | — | — | 3 | 0 | 0 |
| −1 | — | — | — | 6 | 0 | 0 |
| −2 | — | — | — | 9 | 0 | 0 |
| −3 | — | — | — | 12 | 0 | 0 |
| −4 | — | — | — | 15 | 0 | 0 |
| −5 | — | — | — | 18 | 0 | 0 |
| −6 | — | — | — | 21 | 0 | 0 |
| −7 | — | — | — | 24 | 0 | 0 |
| −8 | — | — | — | 27 | 0 | 0 |

Figure 4:
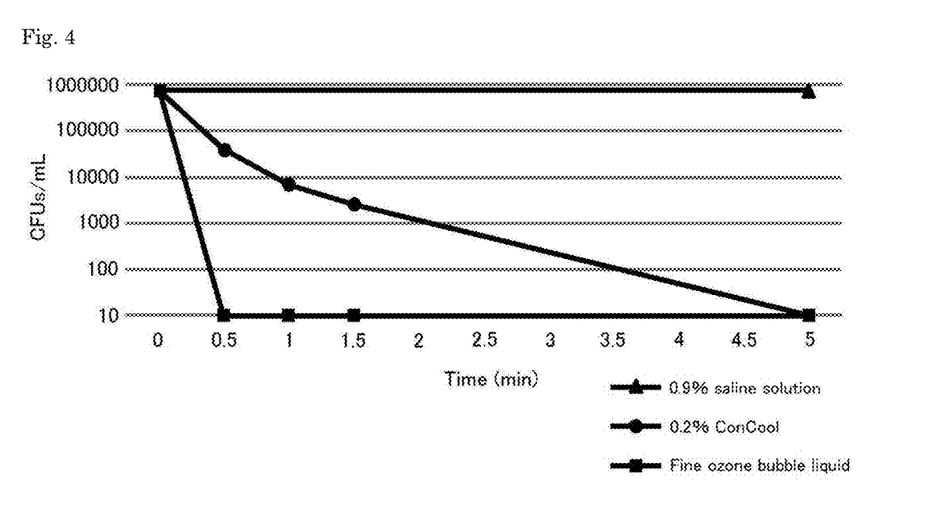
FIG. 4 is a diagram showing the effect of the fine ozone bubble liquid in an immediate effect test of sterilization.

FIG. 4 shows the effect of the fine ozone bubble liquid in an immediate effect test of sterilization. FIG. 4 compares the saline solution having a concentration of 0.9%, an aqueous solution of ConCool (registered trademark), which is sterilizing gargle water, with a concentration of 0.2%, and the fine ozone bubble liquid of embodiment 1. The time required for sterilization until the number of bacteria is 10 or less takes about 5 minutes in ConCool, whereas that of the fine ozone bubble liquid of Embodiment 1 is 1 minute or less. It has been found that the fine ozone bubble liquid of Embodiment 1 has an immediate effect.

Figure 5:
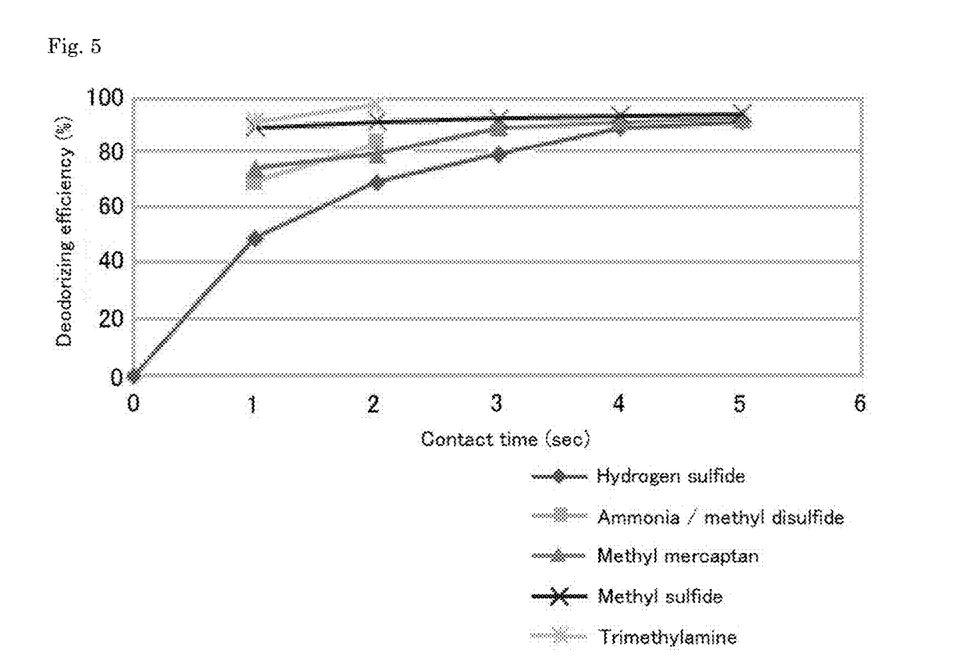
FIG. 5 is a diagram showing the effect of the fine ozone bubble liquid in a halitosis prevention test.

FIG. 5 shows the effect of the fine ozone bubble liquid in a halitosis prevention test. FIG. 5 shows the deodorizing efficiency of the fine ozone bubble liquid of Embodiment 1 with respect to hydrogen sulfide, ammonia/methyl disulfide, methyl mercaptan, methyl sulfide and trimethylamine as odor components. It can be seen that the fine ozone bubble liquid of Embodiment 1 reacts with the odor component in a few seconds and decomposes the source of odor. Furthermore, since the fine ozone bubble liquid of Embodiment 1 can sterilize the bacteria causing the odor, it can be seen that it has a high prevention effect for halitosis.

Further, the safety of the fine ozone bubble liquid of Embodiment 1 has been confirmed. For example, in an experiment in which a high concentration stock solution of 100 ppm or more was orally administered to a rat at 2000 mg/kg of body weight for 14 days, no abnormality was observed in the rat. Thus, the safety of the fine ozone bubble liquid of Embodiment 1 has been confirmed. In addition, it has been proved by a safety test for the oral epithelium and mucosa that the fine ozone bubble liquid of Embodiment 1 is nontoxic.

Figure 6A:
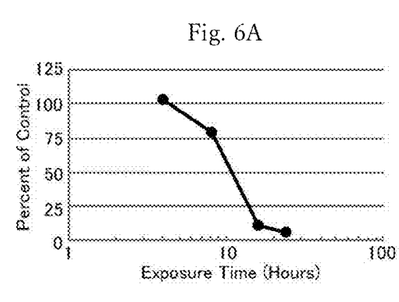
FIGS. 6A to 6D are diagrams showing the result of the safety test compared with ConCool (registered trademark).
Figure 6B:
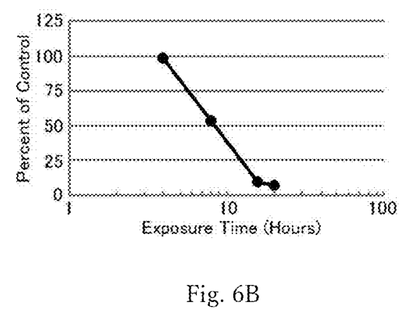
Figure 6C:
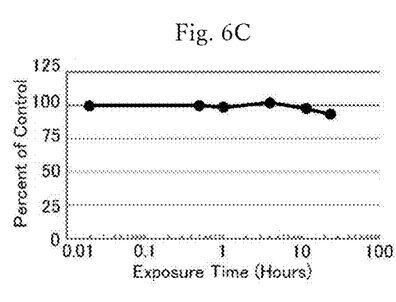
Figure 6D:
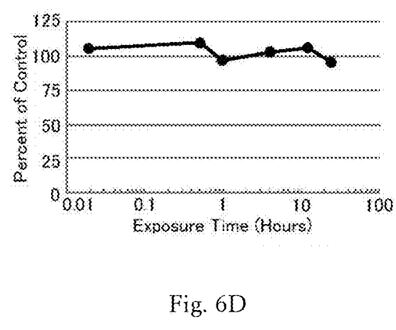

FIGS. 6A to 6D show the result of the safety test in comparison with the ConCool (registered trademark). FIGS. 6A and 6B are the survival rates of tissue cells for chlorhexidine, which is the active ingredient of the ConCool. Different tissue cells are used in FIGS. 6A and 6B. FIGS. 6C and 6D are the survival rates of tissue cells for the fine ozone bubble liquid of Embodiment 1. FIGS. 6C and 6D use the same tissue cells as FIGS. 6A and 6B, respectively. In the case of chlorhexidine, both FIGS. 6A and 6B have been shown to be cytotoxic with time. In a case of FIG. 6A, the 50% survival rate of tissue cells was 10.8 hours. In the case of FIG. 6B, it was 8.4 hours. On the other hand, in the case of the fine ozone bubble liquid of Embodiment 1, as shown in FIGS. 6C and 6D, cytotoxicity is not observed with time, and therefore the safety of the present invention is confirmed.

Table 3 shows the results of the safety test in comparison with Listerine (registered trademark). The time to halve the number of viable cells was 6.2 hours in an oral epithelium and 1.1 hours in an oral mucosa with Listerine. On the other hand, with the fine ozone bubble liquid of Embodiment 1, it was 24 hours or more in an oral epithelium and in an oral mucosa. Therefore, the safety of the present invention is confirmed.

TABLE 3

|  | Time to halve number of viable cells ($ET_{50}$) | |
| --- | --- | --- |
|  | Oral epithelium | Oral mucosa |
| Fine ozone bubble liquid | 24 hours or more | 24 hours or more |
| Listerine (registered trademark) | 6.2 hours | 1.1 hours |
| Detergent | 6.8 hours | 47 minutes |

Embodiment 2

Hereinafter, a method of using the fine ozone bubble liquid according to Embodiment 2 as gargle water will be described. Since the fine ozone bubble liquid used in Embodiment 2 is the same as the fine ozone bubble liquid used in Embodiment 1, the description of common matters is omitted.

According to the method of using the fine ozone bubble liquid as gargle water of Embodiment 2, by using the fine ozone bubble liquid as gargle water, the oral cavity care having a high sterilizing effect can be easily performed. The effects obtained by the method of using the fine ozone bubble liquid of Embodiment 2 as gargle water are the same as those of embodiment 1.

Further, as a result of gargling using the fine ozone bubble liquid of Embodiment 2, the depth of the periodontal tissue pocket of a patient with periodontal disease was significantly improved. For example, the average pocket depths after 4 weeks and after 8 weeks were improved by about 0.3 mm.

In addition, it was confirmed that gargling using the fine ozone bubble liquid of Embodiment 2 has an analgesic effect on stomatitis and an inflammation improving effect.

Embodiment 3

In Embodiment 3, a method of brushing using the fine ozone bubble liquid will be described. Since the fine ozone bubble liquid used in Embodiment 3 is the same as the fine ozone bubble liquid used in Embodiment 1 or 2, the description of the common matters will be omitted.

The method of water brushing using the fine ozone bubble liquid of Embodiment 3 is as follows.
(1) Put the fine ozone bubble liquid of Embodiment 3 into a cup and dilute it with water, for example, tap water to about 10 to 20 times.
(2) Dip the toothbrush in the diluent of (1) to contain the diluent in the toothbrush.
(3) Press the toothbrush containing the diluent of (2) between the teeth and the gums, in other words, at an angle of about 45 degrees against the periodontal pocket.
(4) In the state of (3), shake the toothbrush pressed against the periodontal pocket gently. At this time, not by sliding the toothbrush but by shaking the toothbrush, the bacteria in the periodontal pocket can be removed.
(5) From the second brushing, when containing the diluent in the toothbrush, rinse the toothbrush with water, for example, tap water, and then contain the diluent in the toothbrush. Hereinafter, repeat the steps (2) to (4) until the water brushing is completed for all the teeth.
(6) After the water brushing is completed, apply commercial toothpaste to the toothbrush to polish the teeth.

By performing the water brushing of Embodiment 3, not only plaque on a gingival margin but also plaque in a periodontal pocket, in other words, plaque in a subgingival margin can be removed. Furthermore, since the fine ozone bubble liquid of Embodiment 3 has the same effects as that of embodiment 1, such as the sterilizing effect, the effects of preventing periodontal disease, preventing halitosis and the like can be obtained by performing water brushing. Further, since the fine ozone bubble liquid has an sterilizing effect, the effect of improving halitosis can be obtained without daily water brushing.

The invention claimed is:

1. An oral cavity care system comprising:
   (1) a means for automatically determining a condition of bacteria in a subgingival margin using a phase contrast microscope after treatment of supplying a fine ozone bubble liquid,
   (2) a means for automatically recording a diagnosis result in an electronic medical record,
   (3) a means for displaying information of the electronic medical record wherein
      a stock solution of the fine ozone bubble liquid has ozone concentration of 100 ppm or more,
      even if ozone concentration of the fine ozone bubble liquid is diluted to 4 ppm or less, the fine ozone bubble liquid has a sterilizing action,
      the fine ozone bubble liquid has ozone concentration of 4 ppm or more after frozen storage for one year or more, and
      in addition to the sterilizing action, the fine ozone bubble liquid has an odor component decomposition action and an antiviral action.

2. The oral cavity care system according to claim 1, wherein, in the means (1), the condition of bacteria is automatically determined and on the basis of the determination, the necessity of additional treatment is determined and displayed on the means for displaying information.

3. The oral cavity care system according to claim 1, wherein the condition of bacteria determined in the means (1) is automatically recorded in the electronic medical record and taken into account in a next diagnosis.

4. The oral cavity care system according to claim 1, wherein the information displayed in (3) is supplied to a means for removing tartar or plaque with an ultrasonic scaler while supplying the fine ozone bubble liquid to the tip of the ultrasonic scaler.

5. The oral cavity care system according to claim 1, wherein the fine ozone bubble liquid includes at least one type of fine bubbles among micro bubbles, micro nano bubbles and nano bubbles in a production process.

6. The oral cavity care system according to claim 1, wherein the fine ozone bubble liquid is produced by containing fine bubbles of ozone gas in water in a production process.

7. The oral cavity care system according to claim 1, wherein the fine ozone bubble liquid is used for gargling.

8. The oral cavity care system according to claim 1, wherein the fine ozone bubble liquid is used for brushing.

9. The oral cavity care system according to claim 1, wherein the fine ozone bubble liquid is used for treatment with an ultrasonic scaler.

10. The oral cavity care system according to claim 1, wherein the oral cavity care system is provided for a dental hospital, for treatment of periodontal disease, for preventing periodontal disease or for preventing halitosis.

11. The oral cavity care system according to claim 1, wherein the oral cavity care system is provided for a nursing care facility, a clinic, or gargling in a facility.

12. The oral cavity care system according to claim 1, wherein the oral cavity care system is provided for beauty, health, or sports.

13. The oral cavity care system according to claim 1, wherein the oral cavity care system is provided for a veterinarian, a pet salon, or a pet for improving halitosis.

14. A program, wherein the program operates a computer as each of the means in the oral cavity care system according to claim 1, wherein a storage medium stores the program.

15. An oral cavity care method, comprising:
   improving halitosis in a pet with the oral cavity care system according to claim 1,
   wherein the oral cavity care method is administered by a veterinarian or a pet salon.

* * * * *